(12) United States Patent
Bamberg et al.

(10) Patent No.: US 8,901,515 B2
(45) Date of Patent: Dec. 2, 2014

(54) METHOD FOR NONDESTRUCTIVE TESTING OF WORKPIECE SURFACES

(71) Applicant: MTU Aero Engines GmbH, Munich (DE)

(72) Inventors: Joachim Bamberg, Dachau (DE); Wilhelm Satzger, Munich (DE)

(73) Assignee: MTU Aero Engines GmbH, Munich (DE)

( * ) Notice: Subject to any disclaimer, the term of this patent is extended or adjusted under 35 U.S.C. 154(b) by 34 days.

(21) Appl. No.: 13/745,586

(22) Filed: Jan. 18, 2013

(65) Prior Publication Data

US 2013/0187061 A1     Jul. 25, 2013

(30) Foreign Application Priority Data

Jan. 19, 2012   (DE) .......................... 10 2012 200 767

(51) Int. Cl.
*G01N 21/64* (2006.01)
*G01N 21/91* (2006.01)

(52) U.S. Cl.
CPC ............ *G01N 21/6447* (2013.01); *G01N 21/91* (2013.01)
USPC ...................................................... 250/459.1

(58) Field of Classification Search
CPC ... G01N 21/91; G01N 21/8803; G01N 21/00; G01N 21/6447
USPC ...................................................... 250/459.1
See application file for complete search history.

(56) References Cited

U.S. PATENT DOCUMENTS

| 4,302,678 A | 11/1981 | Schiffert |
| 4,858,465 A * | 8/1989 | Molina ........................... 73/104 |
| 2007/0097360 A1* | 5/2007 | Beaume ..................... 356/237.1 |
| 2007/0267601 A1* | 11/2007 | Zaelke ..................... 252/301.19 |

FOREIGN PATENT DOCUMENTS

| EP | 0 978 719 A1 | 2/2000 |
| EP | 1 048 393 A1 | 11/2000 |
| GB | 819925 | 9/1959 |

* cited by examiner

*Primary Examiner* — Marcus Taningco
(74) *Attorney, Agent, or Firm* — Crowell & Moring LLP

(57) ABSTRACT

A method for nondestructive testing of workpiece surfaces by a fluorescent penetration test is disclosed. An embodiment of the method includes a) cleaning the area of the workpiece surface that is to be inspected; b) applying a fluorescent liquid penetrant to the area of the workpiece surface that is to be inspected, where the penetrant penetrates into possible recesses in the workpiece surface; c) removing the excess penetrant from the workpiece surface; d) applying a developer to the area of the workpiece surface that is to be inspected; e) bleaching the fluorescent penetrant by a beam of light in the layer formed by applying the developer to the workpiece surface; and f) visual evaluation of the fluorescent penetrant remaining in the recesses present in the workpiece surface.

14 Claims, 3 Drawing Sheets

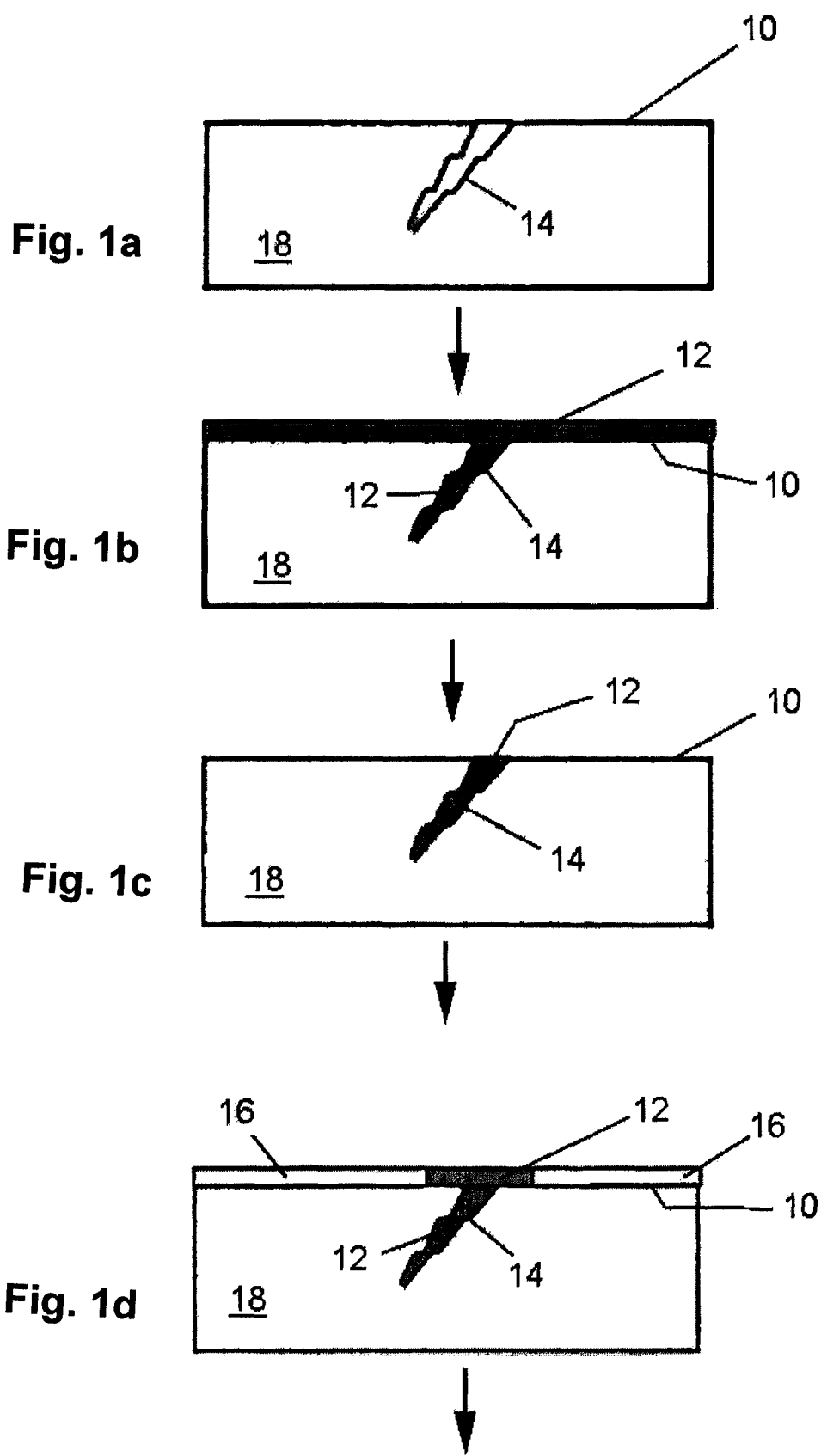

METHOD FOR NONDESTRUCTIVE TESTING OF WORKPIECE SURFACES

This application claims the priority of German Patent Document No. DE 10 2012 200 767.9, filed Jan. 19, 2012, the disclosure of which is expressly incorporated by reference herein.

BACKGROUND AND SUMMARY OF THE INVENTION

The invention relates to a method for nondestructive testing of workpiece surfaces by a fluorescent penetration test.

There are known methods of nondestructive testing of workpiece surfaces. In the so-called penetration test, a penetrant is applied to a cleaned workpiece surface to be inspected. The capillary action of fine surface cracks and pores facilitates the penetration of the penetrant into such recesses in the workpiece surface. The so-called fluorescent penetration test works with a fluorescent penetrant. After a predetermined contact time, excess penetrant is then washed off in an intermediate cleaning operation. Next a developer is applied to the workpiece surface to be inspected. The developer promotes rewetting of the penetrant on the recess of the workpiece surface, so that the developer causes the penetrant to be drawn out of the recess and to the surface. This permits clear visualization of possible irregularities in the workpiece surface, e.g., crack-like separations of material.

The fluorescent penetration test is used in the aeronautical, shipping and automotive engineering industries as well as in metalworking industries in particular. However, other substances such as ceramics can also be inspected for surface cracks and pores accordingly.

However, one disadvantage of the known method for use in aeronautical engineering in particular is that the corresponding areas of the presumed recesses must be surface cleaned manually after application of the developer and after the corresponding mapping of the recesses and/or surface cracks in order to verify the display and remove excess penetrant that has been redistributed on the workpiece surface around the area of the recess by application of the developer. The penetrant, forming a lining only on the recess and/or the surface crack, is visualized only after this mechanical cleaning. An accurate evaluation and measurement of the dimensions of the recess are made possible only in this way. However, this manual cleaning step is time-consuming and cost-intensive. Furthermore, it is very difficult to standardize, so that a standardized classification of possible recesses and/or defects in the workpiece surface is also difficult.

The object of the present invention is to create a method for nondestructive testing of workpiece surfaces which will permit faster and less expensive testing of workpiece surfaces.

The method according to an embodiment of the invention for nondestructive testing of workpiece surfaces by a fluorescent penetration test comprises the following steps:
 a) cleaning the area of the workpiece surface to be inspected;
 b) applying a fluorescent liquid penetrant to the area of the workpiece surface to be inspected, wherein the penetrant penetrates into possible recesses in the workpiece surface;
 c) removing the excess penetrant from the workpiece surface;
 d) applying a developer to the area of the workpiece surface to be inspected;
 e) bleaching the fluorescent penetrant by a beam of light in the layer formed by application of the developer to the workpiece surface; and
 f) visual evaluation of the fluorescent penetrant remaining in the existing recesses in the workpiece surface.

Manual cleaning of the workpiece surface after application of the developer may be omitted through bleaching of the fluorescent penetrant in the developer layer. The corresponding recesses and/or defects, crack-like separations of material, pores and cracks in the workpiece surface are clearly delineated, marked and mapped due to at least partial bleaching of the penetrant, which has been drawn out of the corresponding recesses by the developer and back to the surface of the workpiece. The visual evaluation is performed on the basis of the fluorescent penetrant which is still in the aforementioned recesses, so that the recesses are clearly delineated with respect to the surrounding workpiece surface. Furthermore, some of the penetrant in the recesses is forced back into the developer layer above and/or next to the corresponding recesses due to the osmotic pressure. This advantageously yields a type of magnification effect, which emphasizes the recesses more clearly and makes them recognizable. In addition, some of the penetrant that has not collected in the recesses but instead is adhering to irregularities in the surface of the workpiece or foreign bodies on the surface is reliably bleached, so that the remaining unbleached portions of penetrant clearly indicate the presence of recesses. Manual cleaning of the surface is not necessary. The method according to the invention can be standardized to advantage, thus permitting a classification of possible defects and/or recesses on the workpiece surface which is also standardized. In addition, the method according to the invention can be performed easily, quickly and inexpensively.

In an advantageous embodiment of the method according to the invention, a first visual evaluation of the workpiece surface is performed in a process step d1) prior to the process step e), i.e., bleaching of the fluorescent penetrant. Due to this intermediate step, a first visual inspection of possible recesses and/or defects in the workpiece surface can be performed, so the subsequent bleaching of the fluorescent penetrant is concentrated in the areas of the workpiece surface where possible recesses and/or defects are detected. This may contribute toward better acceleration of the course of the process.

In additional advantageous embodiments of the method according to the invention, the visual evaluation according to process steps f) and/or d1) may be performed by bombarding the workpiece surface to be inspected with UV light. Recesses in the workpiece surface that have been filled and/or wetted with the fluorescent penetrant can be detected distinctly in this way. In addition, it is possible to use an intense UV light for the bleaching process according to process step e). The radiation intensity of the UV light used for bleaching according to process step e) is usually greater than the radiation intensity of the UV light used in process step f) and/or d1). In addition, there is the possibility that the wavelength of the UV light used in the process step e) corresponds to that in process step f) and/or d1). A distinct and accurate visualization of recesses in the workpiece surface is possible due to the UV light used on the one hand, while on the other hand the fluorescent penetrant in the layer formed by applying the developer to the workpiece surface is reliably bleached so that in particular portions of the penetrant that have not accumulated in the recesses but instead are adhering to irregularities in or foreign bodies on the surface of the workpiece are reliably bleached. If UV light of the same and/or a comparable wavelength is used for the visual evaluation and for the bleaching process, then a single UV light source may be used.

In an additional advantageous embodiment of the method according to the invention, the process steps b) through f) are repeated after the end of the process step f). Repeating these process steps may advantageously lead to an even more accurate mapping of unwanted recesses in and/or on the workpiece surface.

In an additional advantageous embodiment of the method according to the invention, the workpiece surface is a surface of a turbo engine, in particular a component of a gas turbine. Components of turbo engines, e.g., an aircraft jet, are especially critical with respect to irregularities on the surfaces of the components, e.g., fine cracks.

In an additional advantageous embodiment of the method according to the invention, the penetrant is a fluorescent dye penetrant. By using a fluorescent dye penetrant, in addition to the display of fluorescence, a color representation of possible recesses in the workpiece surface is also possible. The visual evaluation of the corresponding recesses in the workpiece surface can therefore be performed very easily and very accurately.

The method according to the invention described above is used in particular in the production, final testing and servicing of components of turbo engines, in particular components of a gas turbine.

Additional features of the invention are derived from the claims, the exemplary embodiments and the drawings. The features and combinations of features mentioned in the description as well as the features and combinations of features mentioned below in the exemplary embodiments may be used not only in the particular combination indicated but also in other combinations or alone without going beyond the scope of the present invention.

BRIEF DESCRIPTION OF THE DRAWINGS

FIGS. 1a to 1g show a flow chart of a method according to an embodiment of the invention for nondestructive testing of workpiece surfaces by a fluorescent penetration test.

DETAILED DESCRIPTION OF THE DRAWINGS

Figure 1E:
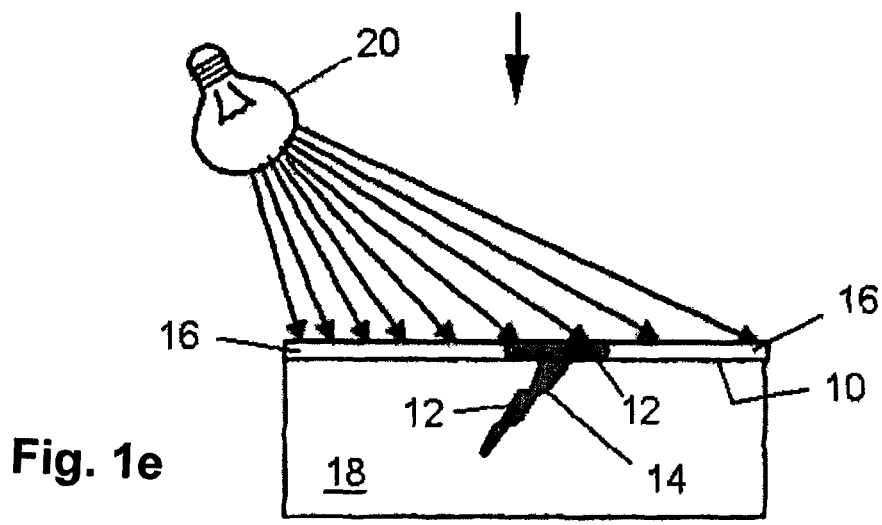

FIGS. 1a to 1g show a flow chart of a method for nondestructive testing of a workpiece surface 10 of a workpiece 18. FIG. 1a shows a workpiece 18 with a workpiece surface 10 and a crack-like recess 14 in the workpiece surface 10. The workpiece surface 10 was cleaned to remove contaminants. FIG. 1b shows the workpiece 18 with a penetrant 12 applied to the workpiece surface 10. This shows that the penetrant 12 also penetrates into the crack-like recess 14 in addition to the layered application to the workpiece surface 10. A liquid fluorescent penetrant 12 is used in the exemplary embodiment illustrated here. A great many corresponding fluorescent penetrants 12 are known from the prior art. Penetrants 12 are used depending on the type of workpiece 18 to be inspected and the material of which it is made; these penetrants have a tendency to spread out not only on the workpiece surface 10 but also into the corresponding recesses 14 in the workpiece surface 10 because of their specifically adjusted properties. Penetrants 12 based on hydrocarbons and organic dyes may be used.

In a subsequent process step, excess penetrant 12 is removed from the workpiece surface 10. The cleaned workpiece surface 10 can be seen in FIG. 1c. The penetrant 12 is present only in the recess 14. In another process step, a developer 16 is applied to the area of the workpiece surface 10 to be inspected. Applying the developer 16 causes the penetrant 12 to be drawn out of the recess 14 and back onto the workpiece surface 10. It is clear from FIG. 1d that now the penetrant 12 is present on the workpiece surface 10 within the developer layer 16, and thus, not only in the recess 14 but also in the areas surrounding the recess 14.

Figure 1F:
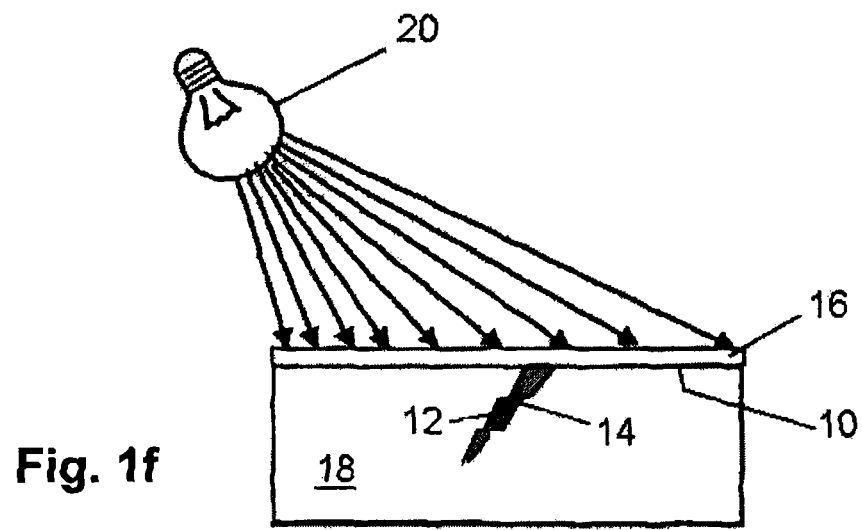

In another process step, the fluorescent penetrant 12 within the layer formed by application of the developer 16 to the workpiece surface 10 is then bleached by a beam of light from a light source 20. UV light of a high radiation intensity is used in the exemplary embodiment shown here. The bleaching is performed until achieving at least partial and even complete bleaching of the fluorescent components within the penetrant 12 in the layer of the developer 16. FIG. 1e shows the start of the aforementioned bleaching process; FIG. 1f shows the end of the bleaching process with complete bleaching of the fluorescent components of the penetrant 12 within the developer layer 16. The developers 16 used are also known from the prior art, but inorganic substances in powder form are generally used.

Figure 1G:
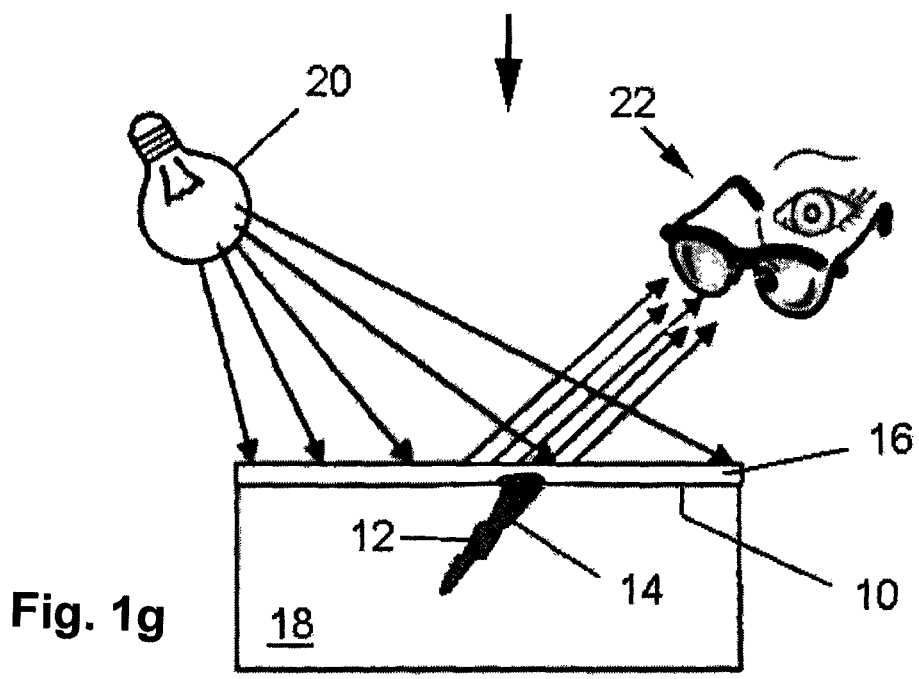

FIG. 1g illustrates the final process step, namely the visual evaluation of the fluorescent penetrant 12 remaining in the recesses 14 present in the workpiece surface 10. The fluorescent penetrant 12 is present only within the crack-like recess 14 due to the previous bleaching process and is no longer present on irregularities or foreign bodies on the workpiece surface 10. The edges of the crack-like recess 14 are marked and can be observed and evaluated accordingly. Furthermore, a portion of the penetrant 12, which is in the recesses is pressed back into the developer layer 16 over and/or next to the recess 14 due to the osmotic pressure. This advantageously results in a type of magnification effect, which definitely emphasizes the recess 14 and makes it discernible.

Any background fluorescence that might be present is eliminated by the bleaching operation depicted in FIGS. 1e and 1f, so that the fluorescent markings and/or areas characterizing the crack-like recesses 14 are clearly discernible.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for nondestructive testing of a workpiece surface by a fluorescent penetration test, comprising the steps of:
   a) cleaning an area of the workpiece surface that is to be inspected;
   b) applying a fluorescent liquid penetrant to the area of the workpiece surface that is to be inspected, wherein a first portion of the penetrant penetrates into a recess in the workpiece surface;
   c) removing a second portion of the penetrant from the workpiece surface that does not penetrate into the recess;
   d) applying a developer to the area of the workpiece surface that is to be inspected and drawing out a portion of the first portion of the penetrant from the recess by the developer;
   e) bleaching the portion of the first portion of the penetrant drawn out from the recess by the developer by a beam of light; and
   f) visually evaluating a remaining portion of the first portion in the recess.

2. The method according to claim 1, further comprising the step of:
   d1) visually evaluating the workpiece surface before step e).

3. The method according to claim 2, wherein the visually evaluating of step f) and/or d1) includes radiating with ultraviolet (UV) light.

4. The method according to claim 1, wherein the bleaching of step e) includes using ultraviolet (UV) light.

5. The method according to claim 2, wherein the visually evaluating of step f) and/or d1) includes radiating with ultraviolet (UV) light, wherein the bleaching of step e) includes using UV light, and wherein a radiation intensity of the UV light of step e) is greater than a radiation intensity of the UV light of step f) and/or d1).

6. The method according to claim 2, wherein the visually evaluating of step f) and/or d1) includes radiating with ultraviolet (UV) light, wherein the bleaching of step e) includes using UV light, and wherein a radiation intensity of the UV light of step e) corresponds to a radiation intensity of the UV light of step f) and/or d1).

7. The method according to claim 1, further comprising the steps of repeating steps b) through f) after step f).

8. The method according to claim 1, wherein the workpiece surface is a surface of a turbo engine.

9. The method according to claim 1, wherein the workpiece surface is a surface of a gas turbine.

10. The method according to claim 1, wherein the penetrant is a fluorescent dye penetrant.

11. A method of producing, final testing, or servicing of a component of a turbo engine comprising the method of claim 1.

12. The method according to claim 11, wherein the turbo engine is a gas turbine.

13. A method for nondestructive testing of a workpiece surface by a fluorescent penetration test, comprising the steps of:
  applying a fluorescent liquid penetrant to an area of the workpiece surface that contains a recess;
  bleaching a first portion of the penetrant on the workpiece surface, wherein the first portion of the penetrant is included within a layer of a developer on the workpiece surface; and
  visually evaluating a second portion of the penetrant in the recess.

14. The method according to claim 13, wherein the bleaching includes using ultraviolet (UV) light.

* * * * *